United States Patent [19]
Nishiguchi et al.

[11] Patent Number: 6,025,310
[45] Date of Patent: Feb. 15, 2000

[54] ORGANIC COMPOUNDS SUITED TO LUBRICATING FILMS ON MAGNETIC RECORDING MEDIA

[75] Inventors: Ikuzo Nishiguchi, Hirakata; Hiroki Hara, Kobe; Sigeru Tsuboi, Amagasaki; Seiki Sugi, Sakai; Kazuhiro Higuchi, Itami, all of Japan

[73] Assignee: Kubota Corporation, Osaka, Japan

[21] Appl. No.: 09/045,591

[22] Filed: Mar. 23, 1998

[30] Foreign Application Priority Data

Aug. 4, 1997 [JP] Japan .................................. 9-208867

[51] Int. Cl.[7] .................. C10M 105/54; C10M 131/10; C07C 43/12
[52] U.S. Cl. .................. 508/582; 508/307; 508/422; 568/633; 568/634; 568/659; 568/660; 568/661; 568/662; 568/663
[58] Field of Search .................... 508/582, 307, 508/422, 633, 634, 659, 660, 661, 662, 663

[56] References Cited

U.S. PATENT DOCUMENTS

| | | | |
|---|---|---|---|
| 2,702,825 | 2/1955 | Ross et al. | 260/611 |
| 3,975,448 | 8/1976 | Delaunois et al. | 260/611 A |
| 4,836,944 | 6/1989 | Tohzaka et al. | 508/582 |
| 5,498,359 | 3/1996 | Shinomoto et al. | 508/582 |
| 5,663,127 | 9/1997 | Flynn et al. | 508/582 |

*Primary Examiner*—Jerry D. Johnson
*Attorney, Agent, or Firm*—Armstrong, Westerman, Hattori, McLeland and Naughton

[57] ABSTRACT

The invention provides novel organic compounds, and more particularly those having excellent lubricity, compatible with lubricating organic compounds having a benzene ring and a phosphazine ring and retaining stability free of hydrolysis for a prolonged period of time. The organic compounds are represented by the formula $R_1$—$R_0$—$R_1$ or $R_0$—$R_1$. $R_0$ is a chain saturated organic group containing a chain of carbon atoms or a chain of carbon atom C and oxygen atom O, and filled with fluorine atoms F or trifluoromethyl groups $CF_3$ except at one end or both ends of the chain. $R_1$ is —$CH_2$—O—$(CH_2)_p$—$\{CH(CH_3)\}_k$—$\{C(CH_3)_2\}_t$—$R_2$ wherein p, k and t are each an integer of 0 or not smaller than 1, and $R_2$ is phenyl or a functional group corresponding to phenyl in which at least one of the hydrogen atoms is substituted with a compound of at least two elements selected from the group consisting of C, H, O and F or with F, Br or Cl.

7 Claims, 8 Drawing Sheets

ORGANIC COMPOUNDS SUITED TO LUBRICATING FILMS ON MAGNETIC RECORDING MEDIA

FIELD OF THE INVENTION

The present invention relates to novel organic compounds, and more particularly to organic compounds having excellent lubricity and suitable especially as lubricants for lubricating films on magnetic recording media.

BACKGROUND OF THE INVENTION

Magnetic recording media (disks) for use in magnetic recording-reproduction devices such as hard disk drives are prepared generally by forming a layer containing at least Ni and P over a nonmagnetic substrate, such as a glass substrate, to obtain a base plate and successively forming over the base plate a ground layer, magnetic layer, protective film and lubricating film.

Improved recording densities are required of magnetic recording media. To give an improved recording density, there is a need to reduce the distance between the head and the disk (head flying or levitation height). It is practice in recent years to hold the head almost in contact with the disk for recording or playback.

When signals are recorded or reproduced in such a quasi-contact state, the disk comes into contact with the head while rotating at a high speed, giving an increased load to the lubricating film of the disk. Consequently the lubricating film or protective film wears away, producing a deposit on the head, permitting the deposit to push up the head to a higher flying level or causing the head to levitate with impaired stability to render the head no longer operable properly for recording or reproduction. It is also likely that the lubricant forming the lubricating film will decompose to exhibit lower lubricity.

The reduction in the head levitation level further results in marked wear upon CSS (Contact, Start and Stop) and is likely to produce increased friction between the head and the disk or to cause damage to the head or the disk.

PFPE (perfluoropolyether) lubricants are known as typical lubricants for magnetic recording media. Examples of such PFPE lubricants include ZDOL (formula #101) and AM3001 (formula #102) commercially available from AUSIMONT in Italy, and DEMNUM SP3 (formula #103) and DEMNUM SA3 (formula #104) commercially available from Daikin Kogyo Co. Ltd. in Japan. These examples of lubricants are all brand names.

$$HOCH_2-\{(CF_2(OC_2F_4)_m-(OCF_2)_n-OCF_2\}-CH_2OH \quad \#101$$

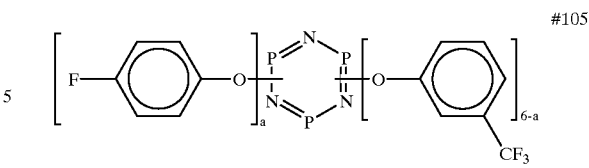

However, these lubricants fail to exhibit satisfactory lubricity during use while the head is in quasi-contact with the disk, and encounter difficulty in giving sufficient resistance to friction and abrasion.

Cyclotriphosphazine (brand name: X-1P, commercially available from Dow Chemical Co.) is used as a lubricant capable of giving high lubricity to the disk in quasi-contact with the head and greatly diminishing the abrasion of the disk and the head. X-1P is an organic compound having benzene rings and a phosphazine ring as represented by the formula #105 given above.

X-1P nevertheless has a molecular weight of about 1000 which is smaller than the conventional PFPE lubricants, and is inferior to the PFPE lubricants in adhesion to the carbon protective film, so that when singly used as a lubricant, X-1P not only spontaneously evaporates but also flows circumferentially off the disk if the disk is rotated for a long time, consequently gradually decreasing in quantity as applied to the disk and making it difficult to assure sufficient lubricity over a prolonged period of time.

Accordingly, it is attempted to admix a very small amount of X-1P with the conventional PFPE lubricant to prepare a lubricant composition for use in the form of a lubricating film. It has been found that the mixture of the PFPE lubricant and X-1P materially lessens the problem of friction between the head and the disk and abrasion thereof involved in the quasi-contact, serving to improve the performance of the disk.

The lubricant composition in the form of a mixture of PFPE lubricant and X-1P exhibits excellent lubricity when the head is in quasi-contact with the disk as stated above, whereas several days or several weeks after the composition is applied in the form of a lubricating film to the disk, the disk develops numerous small spots 12, about 1 μm in diameter and hundreds of nanometers in height, over the surface 10 as shown in FIGS. 1 and 2 to cloud the disk surface. This phenomenon is called "haze", which is produced by X-1P applied onto the disk upon coagulating into small spots 12. It has been found that the haze occurs more frequently in an environment of higher humidity or temperature.

If the spots 12 of the haze become higher than the head flight level, the head collides with the spots during travel,

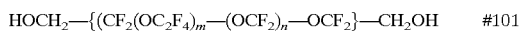

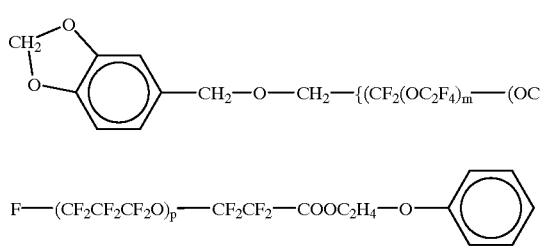

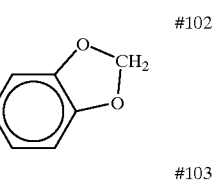

$$F-(CF_2CF_2CF_2O)_p-CF_2CF_2-CH_2OH \quad \#104$$

permitting the lubricant composition to adhere to the surface of the head, or the haze spots will impede the normal travel of the head to result in seriously impaired recording or reproduction ability. There is also the likelihood that the head will be attracted to the disk to hamper the rotation of the disk.

Although the cause of haze still remains to be fully clarified, the present applicant has established that the haze is a phenomenon wherein the PFPE lubricant and X-1P are immiscible and separate each in the original state, forming a coagulation in the form of a thin film, and that the compatibility of the PFPE lubricant and X-1P is governed by the functional group of the PFPE lubricant.

However, AM type lubricants (such as AM3001), even in the original state, are compatible with X-1P, should therefore be less susceptible to hazing than ZDOL, but nevertheless eventually produce haze upon lapse of a long period of time when made into a lubricating film. We have found that the functional group of the AM type lubricant on the disk hydrolyzes mainly to hydroxyl at the portion of the benzyl position as represented by the following formulae, consequently rendering the lubricant no longer compatible with X-1P to result in haze.

Hydrolysis of functional group of AM type lubricant is shown in below:

pounds having a benzene ring and a phosphazine ring and retaining stability free of hydrolysis for a prolonged period of time.

SUMMARY OF THE INVENTION

The organic compounds of the present invention are represented by the general formula $R_1—R_0—R_1$ or $R_0—R_1$.

$R_0$ is a chain saturated organic group containing a chain of carbon atoms or a chain of carbon atom C and oxygen atom O, and filled with fluorine atoms F or trifluoromethyl groups $CF_3$ except at one end or both ends of the chain.

Stated more specifically, when the organic compounds are represented by the general formula $R_1—R_0—R_1$, $R_0$ is a chain saturated organic group represented by $—CF_2—(OCF_2CF_2)_m—(OCF_2)_n—CF_2—$ wherein m and n are each an integer of not smaller than 1. Preferably, m is 10 to 40, and n is 10 to 40.

When the organic compounds are represented by the general formula $R_0—R_1$, $R_0$ is a chain saturated organic group represented by $F(CF_2CF_2CF_2O)_q—CF_2CF_2—$ wherein q is an integer of not smaller than 1, preferably 20 to 80, or a chain saturated organic group represented by

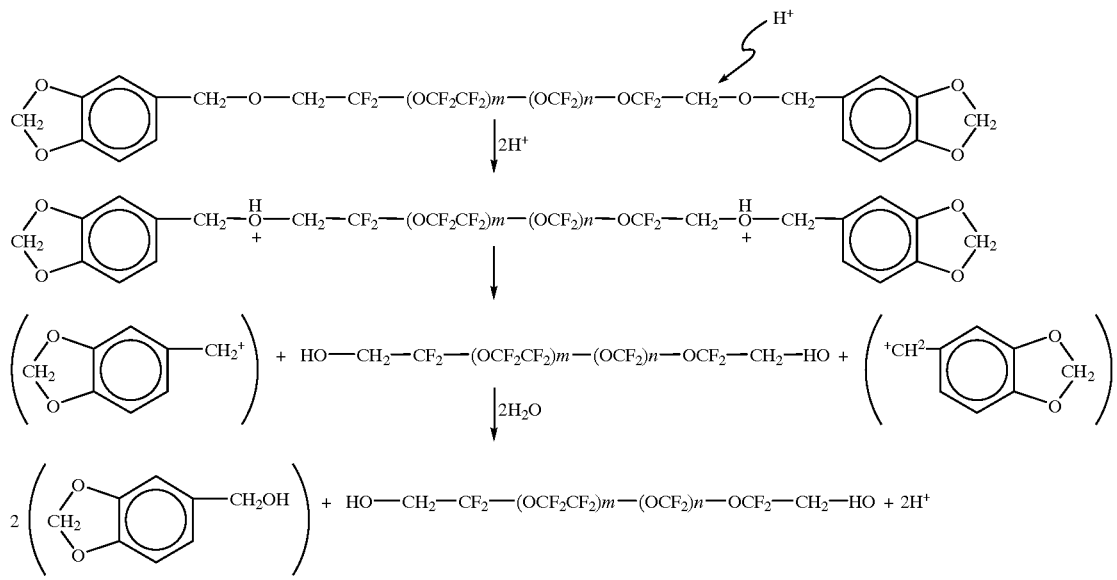

FIG. 3 shows the decomposition of the functional group $—C_8H_7O_2$ of AM3001 on the disk to $—CF_2CH_2OH$ as determined by TOF-SIMS. With reference to FIG. 3, the proportion of the functional group $—C_8H_7O_2$ decreases with time to increase the proportion of the functional group $—CF_2CH_2OH$. In FIG. 3, the initial value for the functional group $—C_8H_7O_2$ at time 0 is taken as 10 as a standard, and the initial value for the functional group $—CF_2CH_2OH$ at time 672 is standardized as 10.

Accordingly, we have developed organic compounds capable of retaining for a prolonged period of time a structure compatible with lubricating organic compounds such as X-1P containing a benzene ring and phosphazine ring by altering the structure of the terminal functional group of lubricants which is responsible for the hydrolysis described, whereby the present invention has been accomplished.

An object of the present invention is to provide novel organic compounds, and more particularly those having excellent lubricity, compatible with lubricating organic com- $F(CF(CF_3)CF2O)_r—CF_2$ $CF_2—$ wherein r is an integer of not smaller than 1, preferably 20 to 80.

$R_1$ is represented by $—CH_2—O—(CH_2)_p—\{CH(CH_3)\}_k—\{C(CH_3)_2\}_t—R_2$ wherein p, k and t are each an integer of 0 or not smaller than 1, p+k+t≧2, and $R_2$ is phenyl or a functional group corresponding to phenyl in which at least one of the hydrogen atoms is substituted with a compound of at least two elements selected from the group consisting of C, H, O and F or with F, Br or Cl. To be suitable, p+k+t is 2 to 10, and preferably p≧2.

Given below are examples of functional groups $R_2$ included in groups $R_1$.

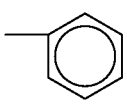 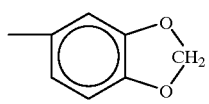

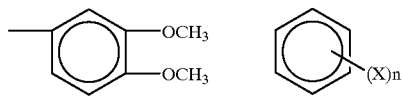
Examples of organic compounds of the present invention are those represented by the following formulae #1 to #24.
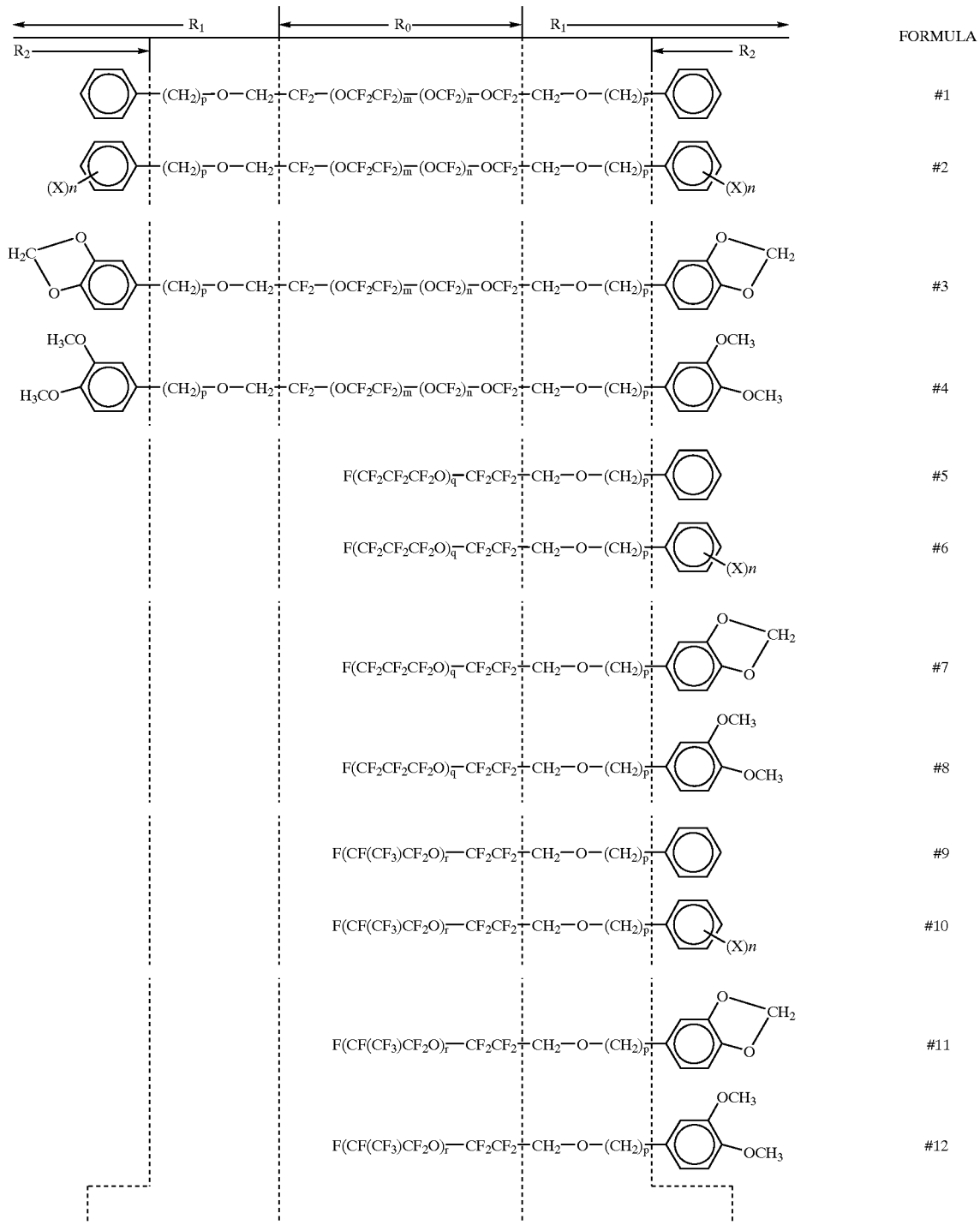

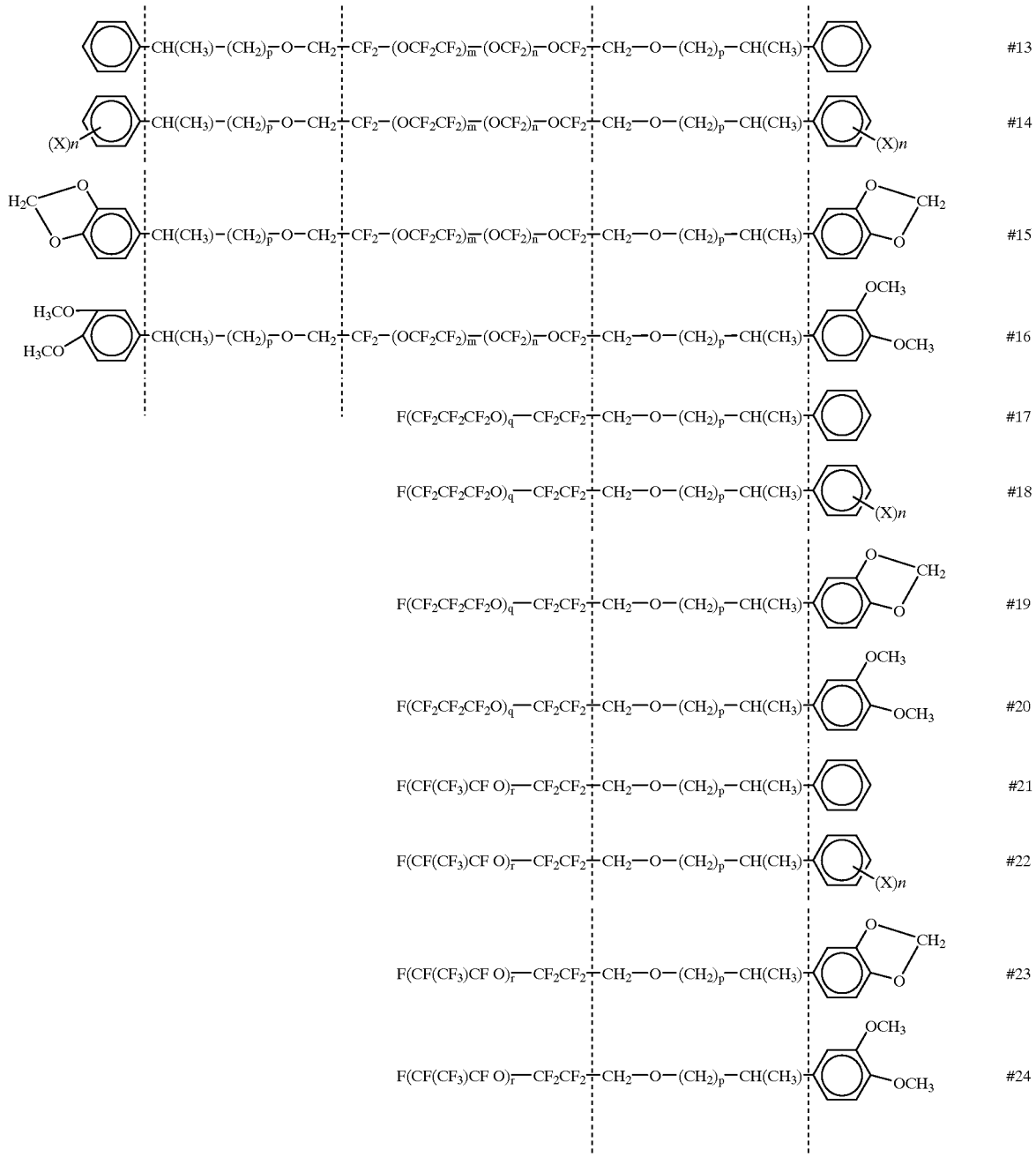

The organic compound of the invention has a straight—chain carbon bond ($-(CH_2)_p-$) between the functional group $R_2$ and the chain organic group $R_0$, so that the functional group $R_2$ in the organic compound remains stable free of hydrolysis.

The organic compound of the invention is suitable for use as a lubricant for the lubricating film of magnetic recording media. The functional group $R_2$ is excellent in adhesion to the carbon protective film of the disk, consequently rendering the lubricant less liable to flow cicumferentially of the disk even if the disk is rotated at a high speed. The compound is free of hydrolysis and will not diminish owing to evaporation, exhibiting stabilized lubricity over a prolonged period of time.

The organic compound of the invention is compatible with lubricating organic compounds having a benzene ring and phosphazine ring (e.g., X-1P) and therefore develops no haze for a long period of time even when used as mixed with the lubricating compound having a benzene ring and phosphazine ring. In the case where the organic compound of the invention is used as mixed with the lubricating organic compound having a benzene ring and phosphazine ring in the form of a lubricating film for the magnetic recording medium, the present compound permits the latter lubricating organic compound to retain its outstanding lubricity while preventing the evaporation and diminution of the latter to ensure high reliability over a long period of time.

DETAILED DESCRIPTION OF THE INVENTION

The organic compounds represented by the foregoing formulae can be prepared by various processes.

<Process for Preparing Organic Compound Represented by the Formula #1>

Figure 1:
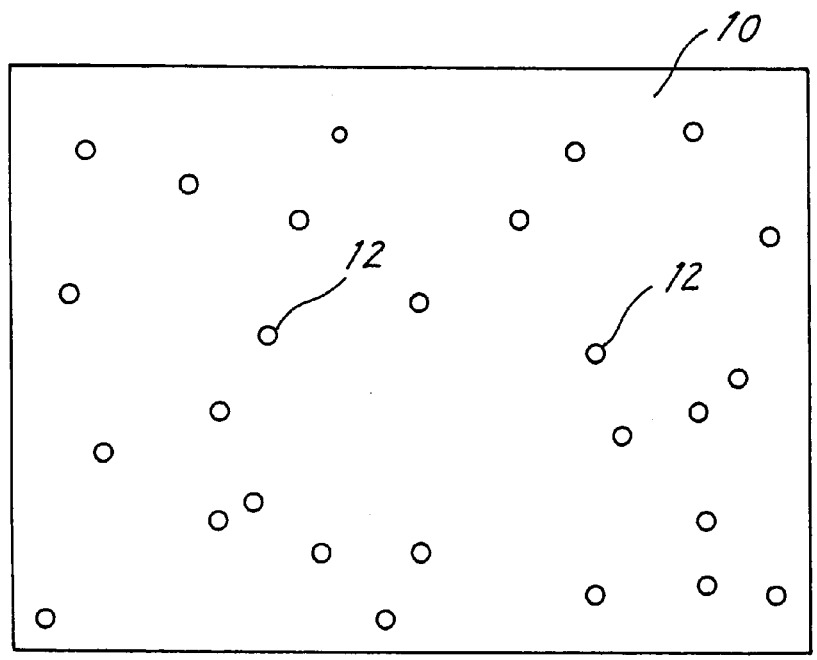
FIG. 1 is a diagram showing haze produced on the surface of a magnetic recording medium and as observed under an optical microscope at a magnification of X500.
Figure 2:
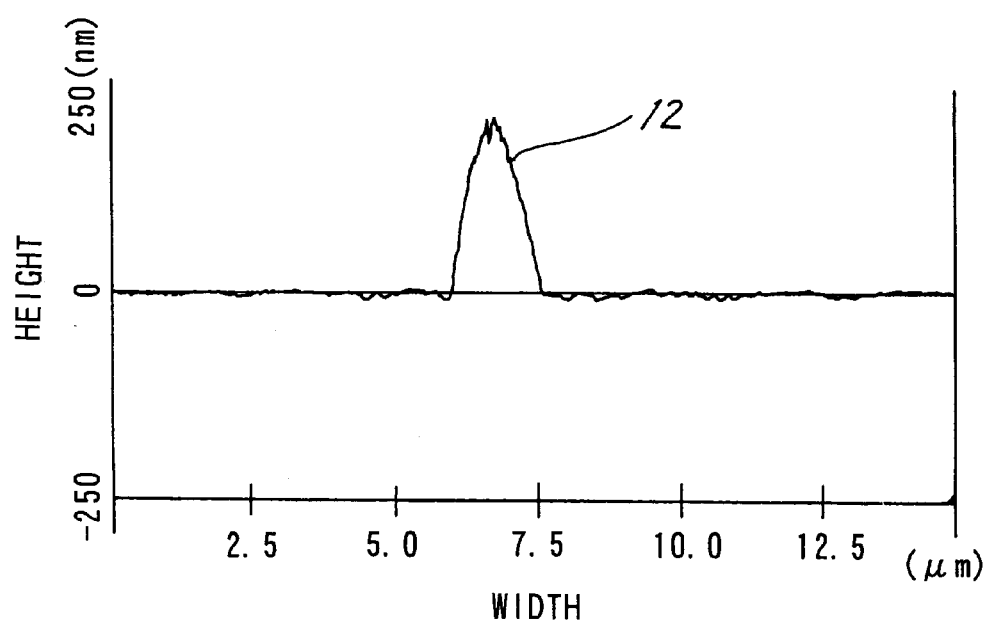
FIG. 2 is an analysis diagram of a haze-forming spot to show the height thereof measured.
Figure 3:
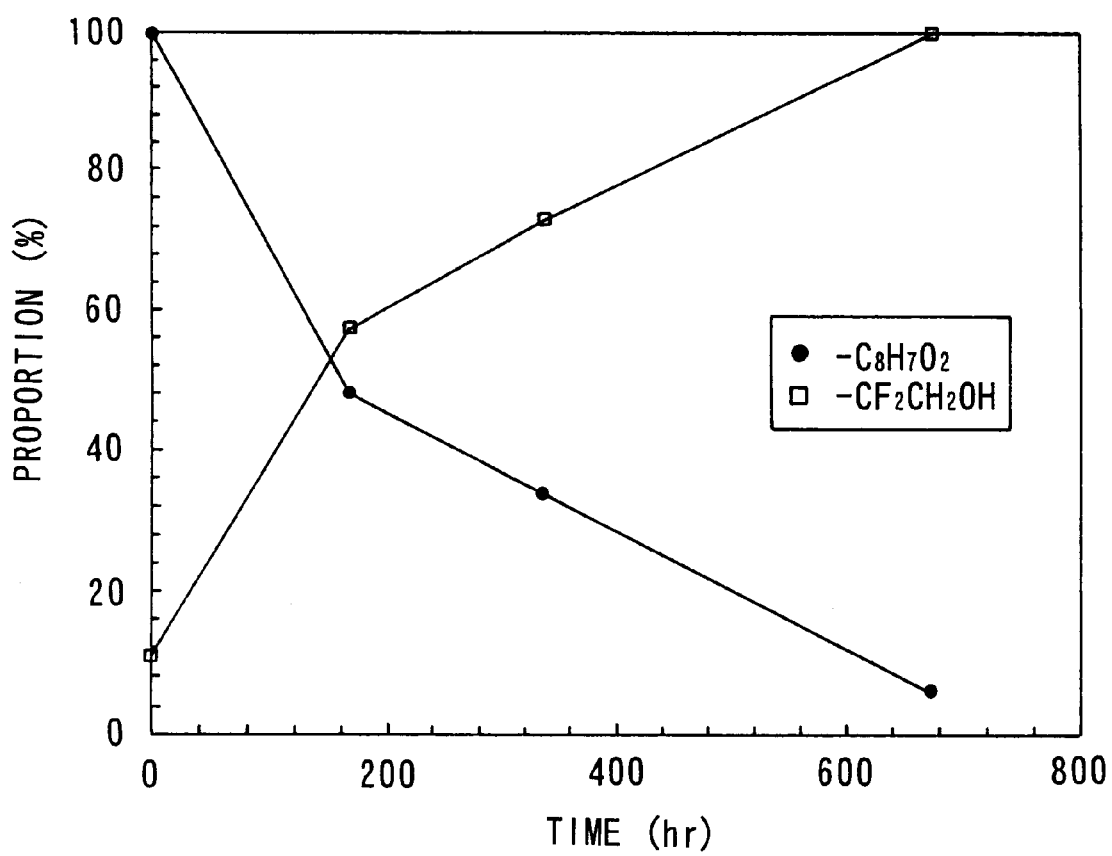
FIG. 3 is a diagram showing the conversion of functional group of AM3001 due to decomposition on a disk, as determined by TOF-SIMS.
Figure 4:
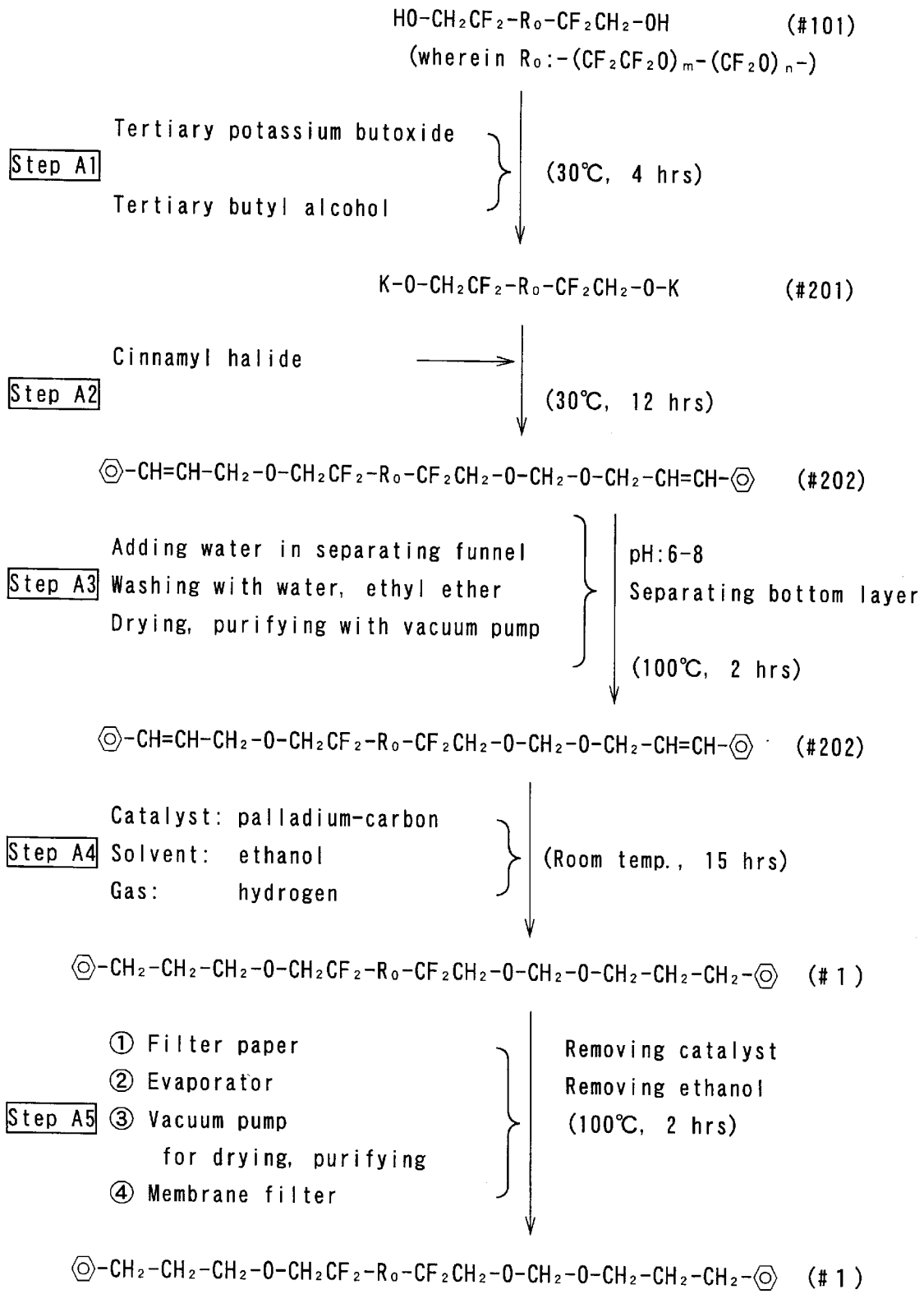
FIG. 4 is a chart showing a process for preparing a compound of the formula #1.

An organic compound represented by the formula #1 is prepared by the process to be described below with reference to FIG. 4.

Step A1

First, ZDOL (molecular weight: 3000, formula #101), product of AUSIMONT in Italy, is prepared. The ZDOL is added to tertiary butyl alcohol solvent containing potassium tertiary butoxide in an amount sufficient for reaction, and the mixture is maintained at 30° C. for 4 hours.

This reaction replaces the terminal H by K, giving a substance of the formula #201.

Step A2

A sufficient amount of a cinnamyl halide is added to the solvent containing the substance of the formula #201, and the mixture is maintained at 30° C. for 12 hours. The reaction replaces the terminal K by —$CH_2$—CH=CH—$C_6H_5$ to produce a substance of the formula #202.

Step A3

The solvent containing the product of Step A2 is transferred to a separating funnel, a large amount of water added to the solvent, and the pH adjusted to 6 to 8, followed by full shaking for mixing. The layer precipitated on the bottom is separated off, washed with water and ethyl ether and thereafter dried and purified at 100° C. for 2 hours using a vacuum pump, whereby the substance of the formula #202 is separated from the solvent.

Step A4

The substance of the formula #202 obtained is placed into ethanol solvent, followed by stirring at room temperature (about 23° C.) for 15 hours for reaction while introducing hydrogen. The catalyst used at this time is palladium-carbon. The reaction saturates the double bonds in the formula #202, creating carbon-hydrogen bonds and producing in the solvent an organic compound of the formula #1 according to the invention.

Step A5

The organic compound (formula #1) of the invention is subsequently collected from the solvent by the following procedure.

The desired compound, i.e., compound of the formula #1, is obtained by (1) separating off the catalyst with filter paper, 2 $\mu$m in pore size, (2) removing the ethanol by an evaporator, (3) subsequently drying and purifying the residue at 100° C. for 2 hours using a vacuum pump, and (4) passing the product through a membrane filter, 0.2 $\mu$m in pore size.

An organic compound represented by the formula #5 can be prepared by using DEMNUM SA3 (formula #104) in place of ZDOL (formula #101) in Step A1. An organic compound represented by the formula #9 can be prepared by using a substance obtained by converting the carboxyl group of F(CFCF$_3$—CF$_2$O)$_m$—C$_2$F$_2$COOH [KRYTOX 157-FSM (brand name), product of E. I. du Pont de Nemours & Co.] to a hydroxyl group in place of ZDOL (formula #101) in Step A1.

<Process for Preparing Organic Compound Represented by the Formula #3>

Figure 5:
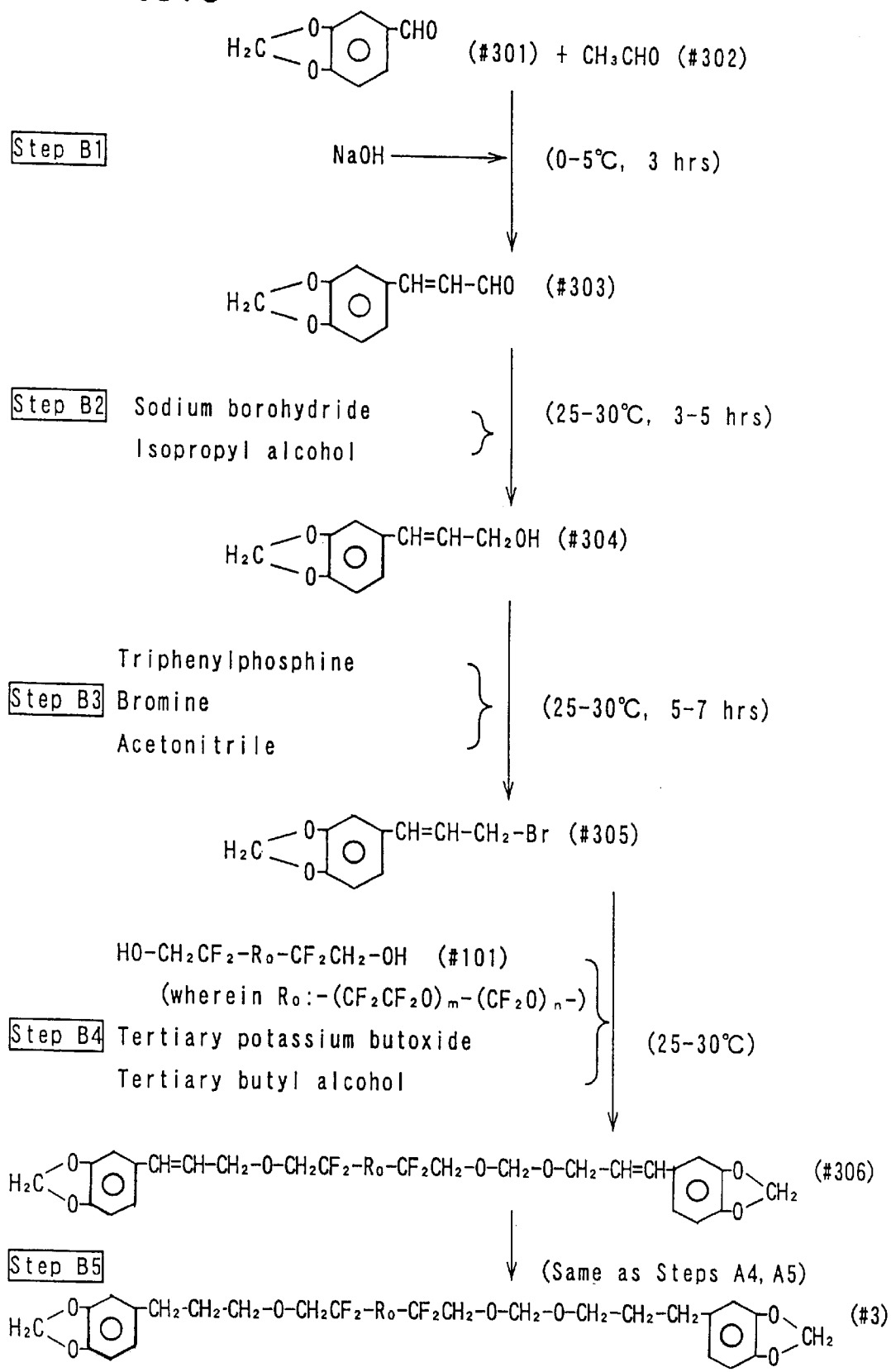
FIG. 5 is a chart showing a process for preparing a compound of the formula #2.

Next, the process for preparing an organic compound of the formula #3 will be described similarly with reference to FIG. 5.

Step B1

First, piperonyl aldehyde (formula #301) and acetaldehyde (formula #302) are added to an aqueous solution of sodium hydroxide (NaOH+H$_2$O), and the mixture is subjected to aldol condensation and dehydration reaction at 0 to 5° C. for 3 hours, giving 3,4-methylenedioxycinnamyl aldehyde (formula #303).

Step B2

The aldehyde obtained is then added to isopropyl alcohol containing sodium borohydride, and the carbonyl group is reduced to an alcohol under the condition of 25 to 30° C. for 3 to 5 hours to obtain 3,4-methylene-dioxycinnamyl alcohol (formula #304).

Step B3

The alcohol obtained is added to acetonitrile containing triphenylphosphine and bromine for reaction at 25 to 30° C. for 5 to 7 hours to obtain 3,4-methylenedioxycinnamyl bromide (formula #305).

Step B4

The bromide (formula #305) obtained is reacted with ZDOL (molecular weight: 3000, formula #101), product of AUSIMONT in Italy in tertiary potassium butoxide and tertiary butyl alcohol at a temperature of 25 to 30° C. to obtain an organic compound represented by the formula #306.

Step B5

The organic compound represented by the formula #3 is prepared by treating the resulting organic compound of the formula #306 in the same manner as in Steps A4 and A5.

An organic compound represented by the formula #7 can be prepared by adding DEMNUM SA3 (formula #104) in place of ZDOL (formula #101) in Step B4. An organic compound represented by the formula #11 can be prepared by adding a substance obtained by converting the carboxyl group of F(CFCF$_3$—CF$_2$O)$_m$—C$_2$F$_2$COOH [KRYTOX 157-FSM (brand name), product of E. I. du Pont de Nemours & Co.] to a hydroxyl group in place of ZDOL (formula #101) in Step B1.

<Process for Preparing Organic Compound Represented by the Formula #4>

Step C

Figure 6:
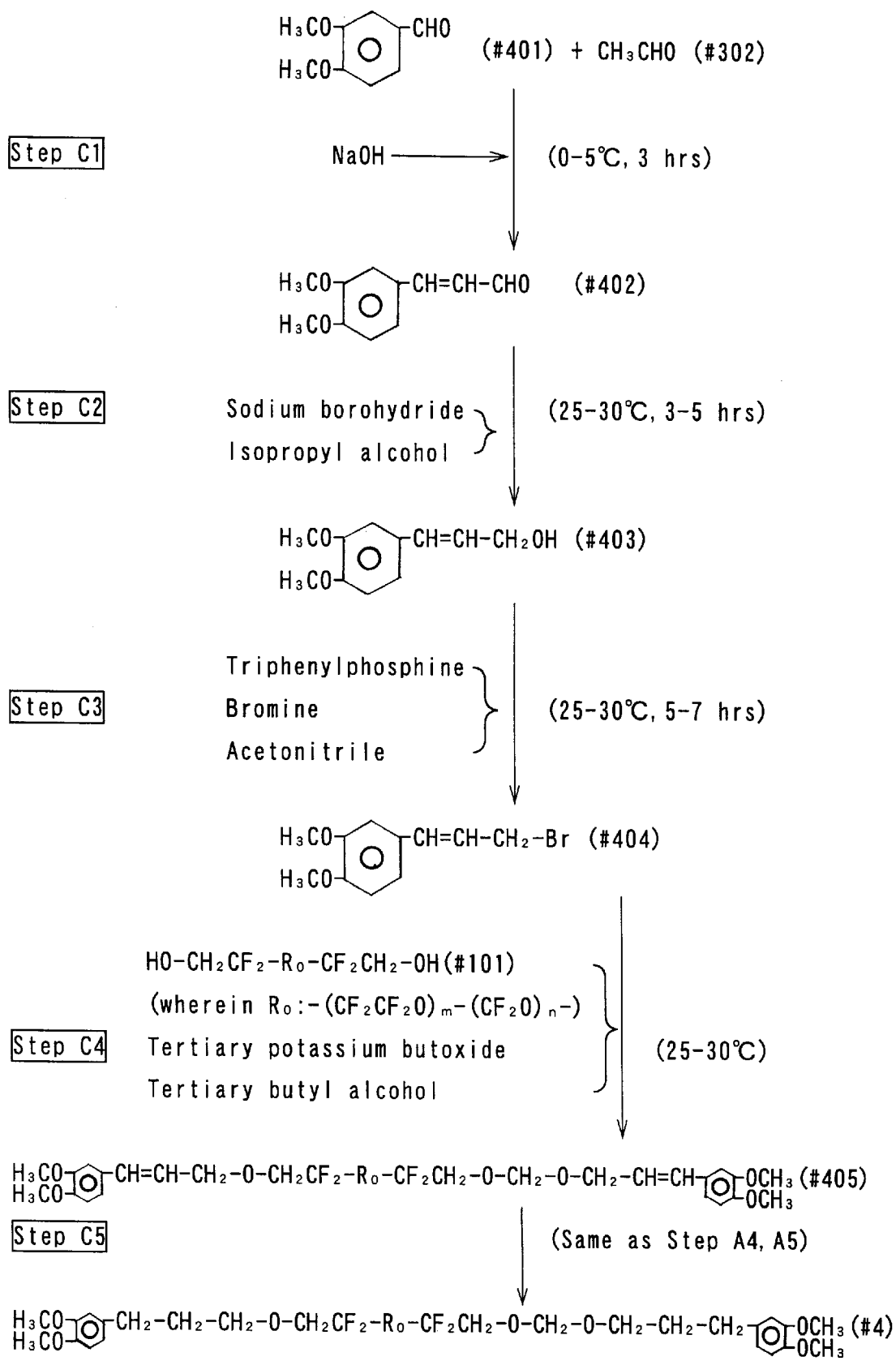
FIG. 6 is a chart showing a process for preparing a compound of the formula #3.

With reference to FIG. 6, an organic compound represented by the formula #4 can be prepared using 3,4-dimethoxybenzaldehyde (formula #401) in place of piperonyl aldehyde (formula #301) of Step B1 and effecting the same reactions as in Steps B. Shown as intermediate products in FIG. 6 are 3,4-dimethoxycinnamyl aldehyde represented by the formula #402, 3, 4-dimethoxycinnamyl alcohol represented by the formula #403, and 3,4-dimethoxycinnamyl bromide represented by the formula #404.

An organic compound represented by the formula #8 can be prepared by adding DEMNUM SA3 (formula #104) in place of ZDOL (formula #101). An organic compound represented by the formula #12 can be prepared by adding a substance obtained by converting the carboxyl group of $F(CFCF_3-CF_2O)_m-C_2F_2COOH$ [KRYTOX 157-FSM (brand name), product of E. I. du Pont de Nemours & Co.] to a hydroxyl group in place of ZDOL (formula #101).

<Process for Preparing Organic Compound Represented by the Formula #15>

Step D1

Figure 7:
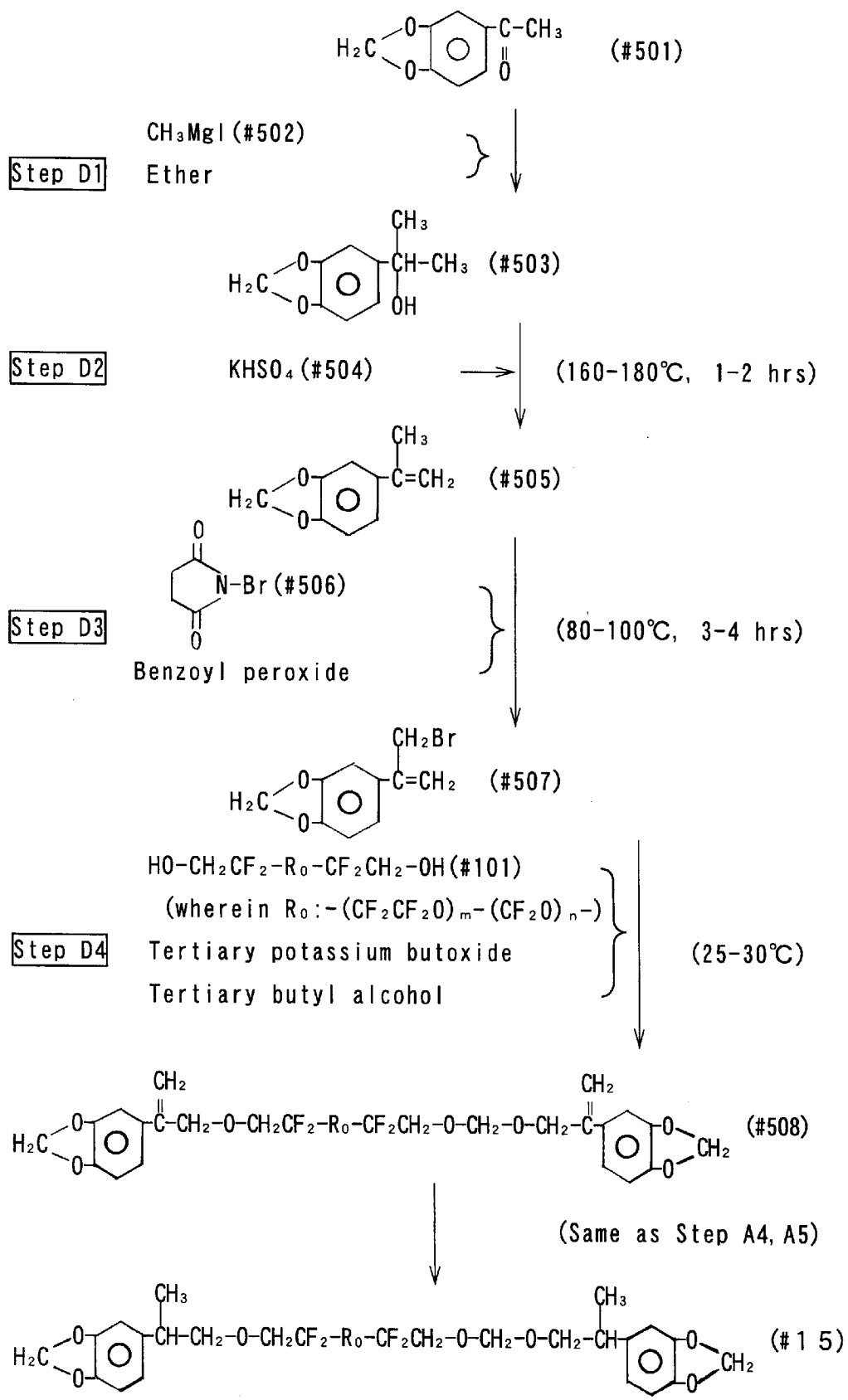
FIG. 7 is a chart showing a process for preparing a compound of the formula #10.

As shown in FIG. 7, 3,4-methylenedioxyacetophenone (formula #501) is reacted in ether containing methylmagnesium iodide (formula #502) to obtain 2-(3,4-methylenedioxyphenyl)propa-2-ol (formula #503).

Step D2

When acidic potassium sulfate (formula #504) is added to 2-(3,4-methylenedioxyphenyl)propa-2-ol (formula #503), a thermal reaction (1-2 hours) at 160–180° C., involving dehydration affords 2-(3,4-methylenedioxyphenyl)propene-2 (formula #505).

Step D3

The resulting 2-(3,4-methylenedioxyphenyl)propene-2 (formula #505) is added to N-bromosuccinimide(formula #506) containing benzoyl peroxide, followed by reaction at 80–100° C. for 3–4 hours whereby 1-bromo-2-(3,4-methylenedioxy)propene-2 (formula #507) is obtained.

Step D4

The 1-bromo-2-(3,4-methylenedioxy)propene-2 (formula #507) obtained is reacted with ZDOL (molecular weight: 3000, formula #101), product of AUSIMONT in Italy, in tertiary butyl alcohol having tertiary potassium butoxide added thereto at a temperature of 25 to 30° C. to produce an organic compound represented by the formula #508.

Step D5

The same procedures as in Steps A4 and A5 thereafter follows to isolate an organic compound represented by the formula #15.

An organic compound represented by the formula #19 can be prepared by adding DEMNUM SA3 (formula #104) in place of ZDOL (formula #101) in Step D4. An organic compound represented by the formula #23 can be prepared by adding a substance obtained by converting the carboxyl group of $F(CFCF_3-CF_2O)_m-C_2F_2COOH$ [KRYTOX 157-FSM (brand name), product of E. I. du Pont de Nemours & Co.] to a hydroxyl group in place of ZDOL (formula #101) in Step D4.

<Process for Preparing Organic Compound Represented by the Formula #13>

Step E

Figure 8:
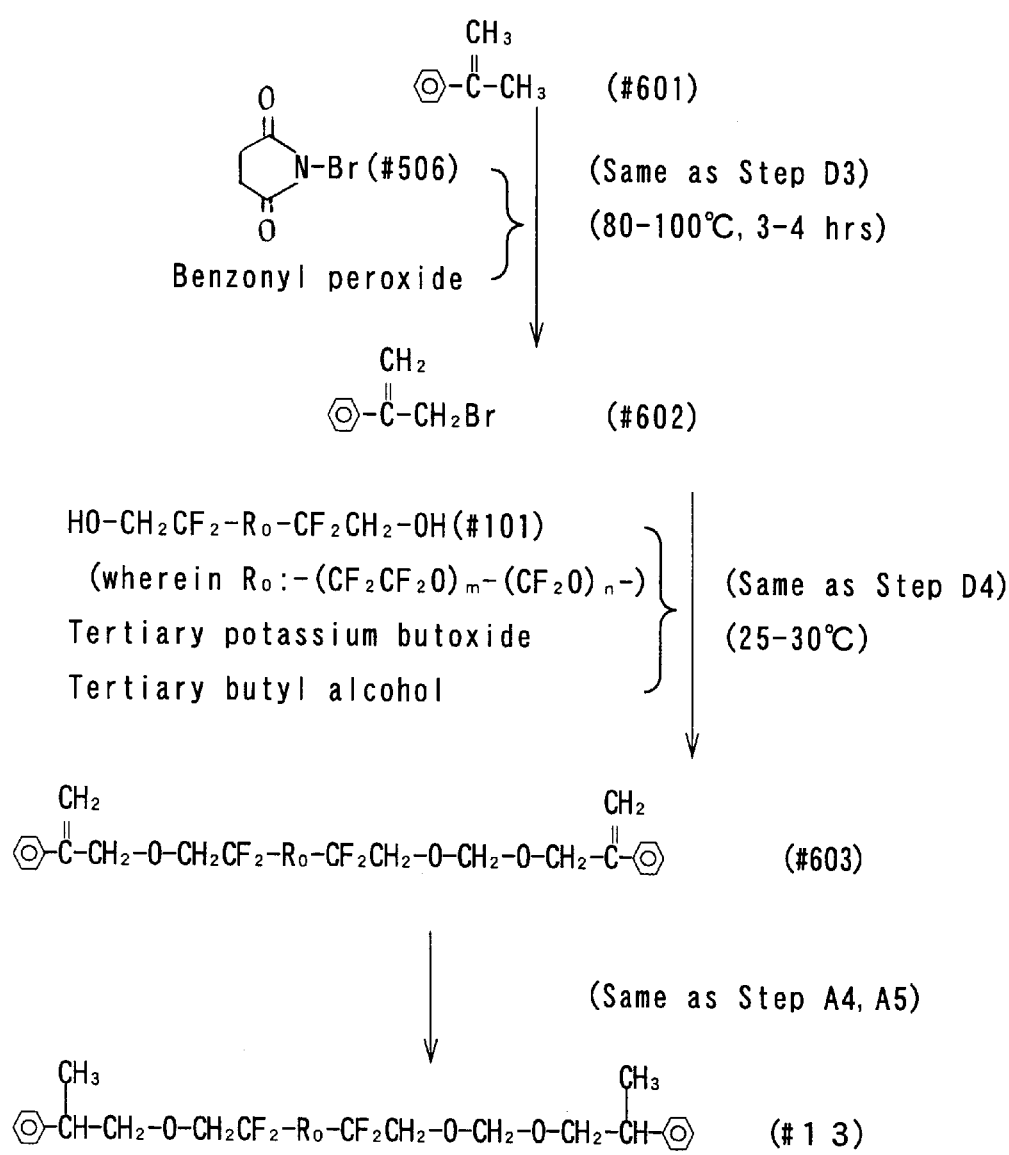
FIG. 8 is a chart showing a process for preparing a compound of the formula #11.

With reference to FIG. 8, an organic compound represented by the formula #13 can be prepared by adding α-methylstyrene (formula #601) in place of 2-(3,4-methylenedioxyphenyl)propene-2 (formula #505) in Step D3, followed by the same procedures as in Steps D4 and D5. The intermediate product of the formula #602 shown in FIG. 8 is 1-bromo-2-phenylpropene-2.

An organic compound represented by the formula #17 can be prepared by adding DEMNUM SA3 (formula #104) in place of ZDOL.

<Process for Preparing Organic Compound Represented by the Formula #16>

Step F

Figure 9:
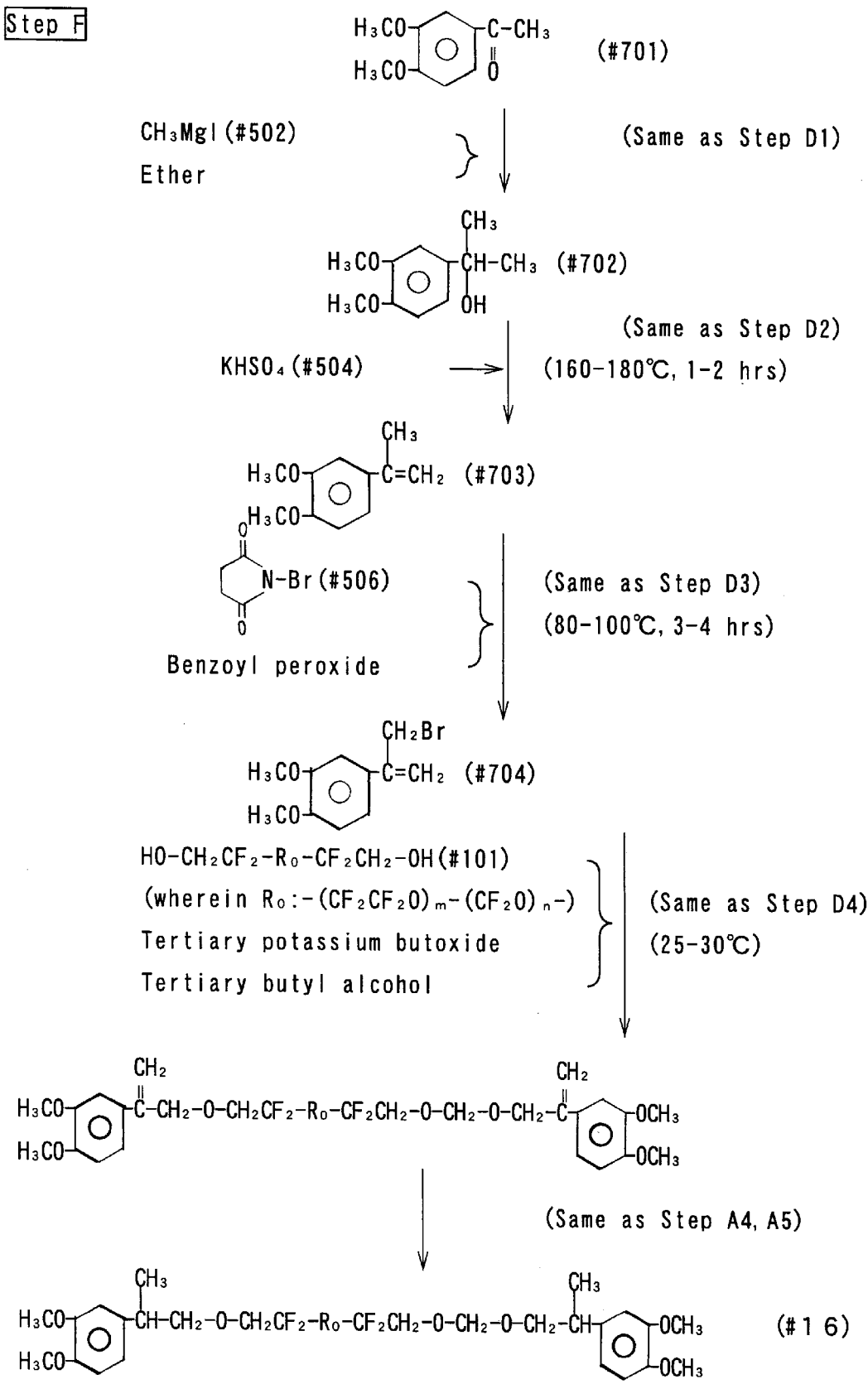
FIG. 9 is a chart showing a process for preparing a compound of the formula #12.

With reference to FIG. 9, an organic compound represented by the formula #16 can be prepared by adding 3, 4-dimethoxyacetophenone (formula #701) in place of 3,4-methylenedioxyacetophenone (formula #501) of Step D1, followed by the same procedures as in Steps D1 to D5. Shown as intermediate products in FIG. 9 are 2-(3,4-dimethoxyphenyl)propa-2-ol represented by the formula #702, 2 -(3, 4-dimethoxyphenyl) propene-2 represented by the formula #703 and 1-bromo-2-(3,4-dimethoxyphenyl) propene-2 represented by the formula #704.

An organic compound represented by the formula #20 can be prepared by adding DEMNUM SA3 (formula #104) in place of ZDOL (formula #101). An organic compound represented by the formula #24 can be prepared by adding a substance obtained by converting the carboxyl group of $F(CFCF_3-CF_2O)_m-C_2F_2COOH$ [KRYTOX 157-FSM (brand name), product of E. I. du Pont de Nemours & Co.] to a hydroxyl group in place of ZDOL (formula #101).

The processes for preparing organic compounds represented by the formulae #2, #6, #10, #14, #18 and #22 will be described with reference to organic compounds having a phenyl group substituted with fluorine at the 3- and 4-positions. The organic compound of the formula #2 can be prepared by reacting 3,4 -difluorocinnamyl bromide with ZDOL (formula #101), product of AUSIMONT in Italy in tertiary potassium butoxide and tertiary butyl alcohol at a temperature of 25 to 30° C. The organic compound of the formula #6 can be prepared by using DEMNUM SA3 (formula #104) in place of ZDOL (formula #101). The organic compound of the formula #10 can be prepared by using a substance obtained by converting the carboxyl group of $F(CFCF_3-CF_2O)_m-C_2F_2COOH$ [KRYTOX 157-FSM (brand name), product of E. I. du Pont de Nemours & Co.] to a hydroxyl group in place of ZDOL (formula #101). The organic compound of the formula #14 can be prepared by reacting 1-bromo-2-(3,4-difluorophenyl)propene-2 with ZDOL (formula #101), product of AUSIMONT in Italy, in tertiary potassium butoxide and tertiary butyl alcohol at a temperature of 25 to 30° C. The organic compound of the formula #18 can be prepared by using DEMNUM SA3 (formula #104) in place of ZDOL (formula #101). The organic compound of the formula #22 can be prepared by using a substance obtained by converting the carboxyl group of $F(CFCF_3-CF_2O)_m-C_2F_2COOH$ [KRYTOX 157-FSM (brand name), product of E. I. du Pont de Nemours & Co.] to a hydroxyl group in place of ZDOL (formula #101).

EXAMPLES

Some of the organic compounds of the invention were each mixed with cyclotriphosphazine (X-1P), and each of the mixtures was applied in the form of a film to a carbon protective film of a magnetic recording medium and checked for lubricity. For comparison, conventional lubricants were mixed with X-1P, and each of the mixtures was similarly made into a lubricating film.

The magnetic recording media to be formed with the lubricating film were prepared under the following conditions.

An NiP layer was formed on an aluminum plate measuring 95 mm in diameter and 0.8 mm in thickness and serving as a substrate, and superpolished to a center line average thickness Ra of 1 nm.

The substrate was mechanically textured by circumferential polishing over the data zone thereof using a diamond slurry, 0.5 μm in mean particle size, and textured by a laser over the CSS zone thereof to form annular projections, 7 μm in diameter and 15 nm in height, at an interval of 30 μm in both radial and circumferential directions.

The substrate thus textured was cleaned with use of a neutral detergent, and a Cr ground layer (40 nm in thickness), CoCrTa magnetic layer (100 G μm) and carbon protective film (10 nm) were successively formed on the substrate by sputtering to prepare a magnetic recording medium.

The lubricants of the formulae shown in Table 1 (examples of the invention: formulae #1, #2, #3 and #4; comparisons: formulae #102 and #101) were each mixed with X-1P in the following manner. The lubricant of the formula #2 prepared for use was one wherein the hydrogen at the 3- and 4-positions of the phenyl was substituted with fluorine.

The lubricant and X-1P, each in an amount of 2 gf, were placed into a mixer, forcibly mixed together with application of ultrasonic waves, then allowed to stand for 24 hours and thereafter checked for compatibility by the eye. As a result, the lubricants other than the one represented by the formula #101 were found to be compatible with X-1P.

The magnetic recording media were immersed in the lubricant composition comprising the lubricant and X-1P mixed therewith to form a lubricating film with a thickness of 2 nm over the surface of each medium.

the foregoing chart showing the hydrolysis of functional group of the AM type lubricant.

On the other hand, the lubricants of Examples 1 to 4 have between the functional group and the chain organic group a straight-chain carbon bond, $(-(CH_2)_p-)$, which renders the functional group less susceptible to hydrolysis.

Critical X-1P Content Without Causing Haze

Magnetic recording media were prepared, with lubricating films formed thereon which had a specified thickness but contained varying amounts of X-1P. The media were allowed to stand in a clean room at a temperature of 23° C. and humidity of 55% for 2 weeks and then checked for haze over the data zone. The lubricating films developing haze were checked for the amount (atomic percent) of phosphorus present in the X-1P in the film by XPS (X-ray photoelectronic spectroanalyzer). Table 1 shoes the result.

Table 1 reveals that a larger amount of X-1P was incorporated in each medium of Examples 1 to 4, as compared with those of Comparisons 1 and 2.

Thus, the result obtained indicates that the lubricants (formulae #1 to #4) of the invention remained stable without developing haze even when mixed with a large amount of X-1P. In contrast, it was found that the conventional lubricants (formulae #102 and #101) rendered the lubricant composition unstable to permit hazing if mixed with a large amount of X-1P.

TABLE 1

| | Example 1 | Example 2 | Example 3 | Example 4 | Comparison 1 | Comparison 2 |
|---|---|---|---|---|---|---|
| Lubricant Composition | formula #1 + X-1P | formula #2 + X-1P | formula #3 + X-1P | formula #4 + X-1P | formula #102 + X-1P | formula #101 + X-1P |
| Compatibility with X-1P | Good | Good | Good | Good | Good | Separated |
| Decomposition ratio of Functional Group | <3% | <3% | <3% | <3% | 97% | <3% |
| Haze-free Critical X-1P Content | 0.75% | 0.36% | 0.82% | 0.79% | 0.08% | 0.05% |
| 70% Value of Haze-free Critical X-1P Content | 0.53% | 0.25% | 0.57% | 0.55% | 0.06% | 0.04% |
| TAA Deterioration | 2.7% | 4.2% | 2.1% | 3.1% | 35.2% | 42.8% |
| Friction Coefficient before CSS | 0.56 | 0.61 | 0.56 | 0.61 | 0.51 | 0.53 |
| Friction Coefficient after CSS | 0.78 | 0.78 | 0.81 | 0.85 | 1.02 | 1.23 |
| Amount of Spin-Off | 3.2% | 3.8% | 3.5% | 4.2% | 2.8% | 4.1% |
| Amount of Evaporation | 4.7% | 5.9% | 5.2% | 5.3% | 4.1% | 5.8% |
| Corrosion | no problem | no problem | no problem | no problem | no problem | no problem |

The media had their lubricating films mechanically polished with a tape and were thereafter subjected to a glide test at a level of 25 nm and to a certify test wherein an inductive try pad head carrying a 50% slider was caused to travel at a level of 38 nm. The magnetic recording media, which were found acceptable by the slide test and the certify test, were further tested by the following methods.

Measurement of Functional Group Decomposition Ratio

The lubricant composition as applied to the magnetic recording medium was allowed to stand in a clean room at a temperature of 23° C. and humidity of 55% for 1 month and then checked by TOF-SIMS for the ratio (decomposition ratio) of functional groups separating from the lubricant. Table 1 shows the result.

With reference to Table 1, the compositions of Examples 1 to 4 and Comparisons 2 were less than 3% in functional group decomposition ratio, hence little or no decomposition. Comparison 1 was 97% in functional group decomposition ratio, this,indicating that almost all functional groups were decomposed. This result is thought attributable to the progress of hydrolysis at the benzyl position as illustrated in To make the lubricating film free from haze over a prolonged period of time, it is desired that the amount of X-1P be up to about 70% of the critical X-1P content which does not cause haze. Said desirable amount of X-1P content which does not cause haze is also described in Table 1 as referring to 70% value of haze-free critical X-1P content.

Seek Test

A head was caused to repeatedly perform a seeking movement radially of the magnetic recording medium for 38 hours while rotating the medium at a temperature of 40° C. and RH of 80%. Before and after the seeking operation, the medium was checked for magnetic signal intensity (TAA) by causing the head, i.e., a try pad head carrying a 50% slider, to travel at a levitation or flight level of 38 nm under a load of 3 gf and recording or reproducing signals of 15 μHz to measure the variations in TAA due to the seeking operation in the high-temperature high-humidity atmosphere. The result is expressed in. percentage in Table 1.

With reference to Table 1, the media of Examples 1 to 4 were several percent in the variations of TAA resulting from the seeking operation, whereas those of Comparisons 1 and 2 exhibited a deterioration of more than 35%. This means that although the heads used for Comparisons 1 and 2 were deteriorated by the seeking operation in the high-temperature high-humidity atmosphere, the heads for Examples 1 to 4 remained almost free of deterioration by virtue of high lubricity of the media.

Variation in Friction Coefficient Due to CSS

The magnetic recording medium was used for CSS at a temperature of 40° C. and RH of 80% to measure variations in the frictional force between a head and the medium.

Using the same head as used for the seek test, the coefficient of friction was measured before and after performing the CSS test 30,000 times in the high-temperature high-humidity atmosphere. Table 1 shows the result.

With reference to Table 1, all the recording media were comparable in the coefficient of friction before the CSS tests. On the other hand, in terms of the coefficient of friction resulting from 30,000 repetitions of the CSS test, the impairment of CSS performance was limited to about 1.5 times the original value in the case of Examples 1 to 4, but was at least about twice the original value in the case of Comparisons 1 and 2. As is the case with the foregoing test, this means that CSS in the humid atmosphere wore the media and heads of Comparisons 1 and 2 to entail an increased frictional force, whereas the lubricant compositions of Examples 1 to 4 permitted little or no increase in the frictional force, exhibiting high lubricity.

Spin-Off Test

The magnetic recording medium was held in rotation at 10,000 rpm for 1 month, and the amount of the lubricating composition thrown off toward the outer periphery (amount of spin-off) was measured. The thickness of film of the lubricant composition was measured by FT-IR. The variation in the film thickness due to the rotation was expressed in percentage. Table 1 shows the result.

Table 1 reveals that all the media were comparable in the amount of spin-off.

Evaporation Test

Magnetic recording media were allowed to stand in an atmosphere having a temperature of 80° C. for 1 month, and the amount of evaporation of the lubricant composition was measured. The film thickness was measured by FT-IR before and after the standing. The average reduction in the film thickness was expressed in percentage. The result is given in Table 1.

Table 1 shows that all the media were comparable in the amount of evaporation of the lubricant composition.

Determination of Corrosion Characteristics

The magnetic recording medium was allowed to stand in an environment having a temperature of 80° C. and humidity of 90% for 2 weeks, then inspected by the eye and subjected to the glide test and certify test previously described, and thereby checked for variations in properties and performance to determine whether the magnetic layer developed corrosion. The result is given in Table 1, which reveals that all the media were free of problems.

As described above, the organic compounds of the present invention are excellent in lubricity, remain stable and free of hydrolysis over a prolonged period of time, and less susceptible to hazing even when used as mixed with other lubricating organic compound (such as X-1P) containing a benzene ring and phosphazine ring.

Although only four of the organic compounds of the invention were tested in the foregoing examples for the evaluation of lubricity and other properties, we have found that the other organic compounds not shown in the examples also have the same properties as described above.

Apparently, the present invention can be modified or altered by one skilled in the art without departing from the spirit of the invention. Such modifications or alterations are included within the scope of the invention as set forth in the appended claims.

What is claimed is:

1. An organic compound represented by a general formula $R_1$—$R_0$—$R_1$ wherein $R_0$ is —$CF_2$—$(OCF_2CF_2)_m$—$(OCF_2)_n$—$CF_2$— wherein m and n are each an integer not smaller than 1, and $R_1$ is —$CH_2O$—$(CH_2)_p$—$\{CH(CH_3)\}_k$—$\{C(CH_3)_2\}_t$—$R_2$ wherein p, k and t are each an integer of 0 or not smaller than 1, $p+k+t \geq 2$, and $R_2$ is phenyl or a functional group corresponding to phenyl in which at least one of the hydrogen atoms is substituted with a compound of at least two elements selected from the group consisting of C, H, O and F or with F, Br or Cl.

2. A lubricating composition for forming a lubricating film on magnetic recording media, wherein said lubricating composition contains an organic compound according to claim 1.

3. A lubricating composition according to claim 2, wherein said lubricating composition further contains an organic lubricant containing at least a benzene ring and a phosphazine ring, said organic compound being mixed with said organic lubricant.

4. A method for lubricating a magnetic recording media, comprising a step of forming a lubricating film on the recording media with a composition according to claim 3.

5. A method for lubricating a magnetic recording media, comprising a step of forming a lubricating film on the recording media with a composition according to claim 2.

6. An organic compound represented by a general formula $R_0$—$R_1$ wherein $R_0$ is $F(CF_2CF_2CF_2O)_q$—$CF_2CF_2$— wherein q is an integer not smaller than 1, and $R_1$ is —$CH_2O$—$(CH_2)_p$—$\{CH(CH_3)\}_k$—$\{C(CH_3)_2\}_t$—$R_2$ wherein p, k and t are each an integer of 0 or not smaller than 1, $p+k+t \geq 2$, and $R_2$ is phenyl or a functional group corresponding to phenyl in which at least one of the hydrogen atoms is substituted with a compound of at least two elements selected from the group consisting of C, H, O and F or with F, Br or Cl.

7. An organic compound represented by a general formula $R_0$—$R_1$ wherein $R_0$ is $F(CF(CF_3)CF_2O)_r$—$CF_2CF_2$— wherein r is an integer not smaller than 1, and $R_1$ is —$CH_2O$—$(CH_2)_p$—$\{CH(CH_3)\}_k$—$\{C(CH_3)_2\}_t$—$R_2$ wherein p, k and t are each an integer of 0 or not smaller than 1, $p+k+t \geq 2$, and $R_2$ is phenyl or a functional group corresponding to phenyl in which at least one of the hydrogen atoms is substituted with a compound of at least two elements selected from the group consisting of C, H, O and F or with F, Br or Cl.

* * * * *